United States Patent
Aita et al.

(10) Patent No.: US 6,884,234 B2
(45) Date of Patent: Apr. 26, 2005

(54) FOLDABLE AND REMOTELY IMAGEABLE BALLOON

(75) Inventors: Michael Aita, Shorewood, WI (US); Milan Mursec, Milwaukee, WI (US)

(73) Assignee: Cardio Exodus Partners, Shorewood, WI (US)

( * ) Notice: Subject to any disclaimer, the term of this patent is extended or adjusted under 35 U.S.C. 154(b) by 182 days.

(21) Appl. No.: 10/002,406

(22) Filed: Nov. 1, 2001

(65) Prior Publication Data

US 2003/0083579 A1 May 1, 2003

(51) Int. Cl.[7] .................. A61M 31/00; A61M 29/00
(52) U.S. Cl. .................. 604/103.01; 604/96.01
(58) Field of Search .................. 604/96.01, 103.1, 604/103.06, 103.11, 103.12, 103.13, 103.14

(56) References Cited

U.S. PATENT DOCUMENTS

| | | | |
|---|---|---|---|
| 4,702,252 A | | 10/1987 | Brooks et al. |
| 5,209,799 A | * | 5/1993 | Vigil ........................... 156/156 |
| 5,304,197 A | * | 4/1994 | Pinchuk et al. .............. 606/194 |
| 5,320,634 A | * | 6/1994 | Vigil et al. .................. 606/159 |
| 5,713,913 A | * | 2/1998 | Lary et al. ................... 606/159 |
| 5,759,174 A | * | 6/1998 | Fischell et al. ............... 604/96 |
| 5,868,704 A | | 2/1999 | Campbell et al. |
| 6,652,568 B1 | | 11/2003 | Becker et al. |
| 2002/0198559 A1 | * | 12/2002 | Mistry et al. ............... 606/194 |

FOREIGN PATENT DOCUMENTS

WO        WO 93/20881        10/1993

OTHER PUBLICATIONS

International Search Report for PCT/US93/03352, mailed May 16, 2003.

* cited by examiner

*Primary Examiner*—Sharon Kennedy
(74) *Attorney, Agent, or Firm*—Edward J. Lynch; Duane Morris LLP

(57) ABSTRACT

The present invention is directed to a polymeric balloon for an intracorporeal catheter having a plurality of spaced apart, remotely imageable layers which facilitate the folding of the balloon. The imageable layer may facilitate imaging the balloon or a portion thereof preferably by fluoroscopic or magnetic resonance based remote imaging systems.

16 Claims, 2 Drawing Sheets

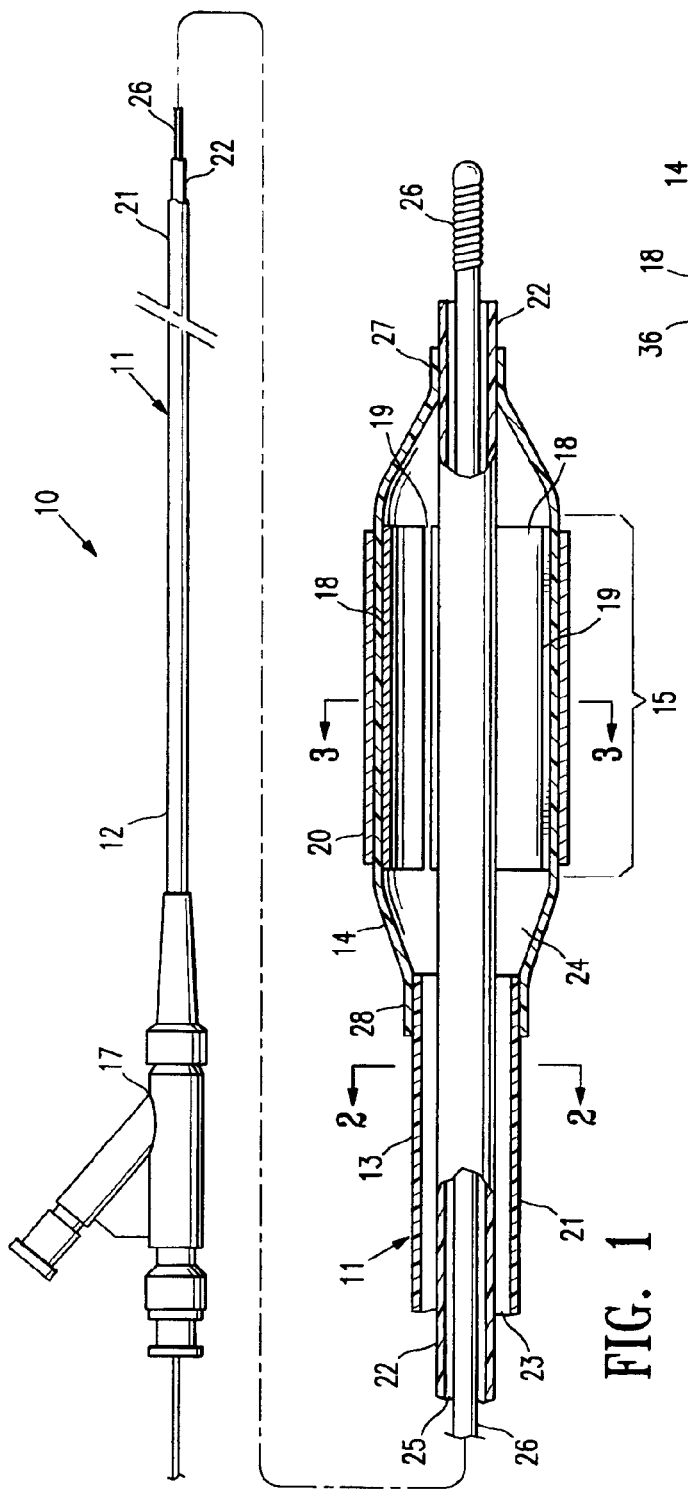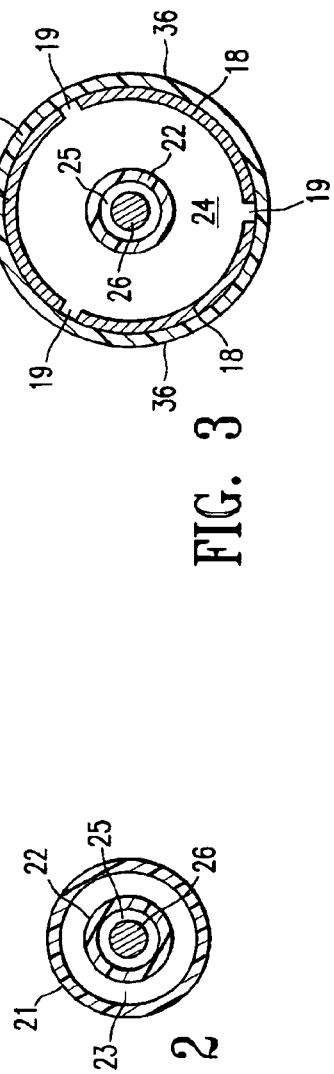

FOLDABLE AND REMOTELY IMAGEABLE BALLOON

BACKGROUND OF THE INVENTION

This invention generally relates to intravascular balloon catheters for procedures such as percutaneous coronary transluminal angioplasty, (PTCA), and particularly to a balloon catheter for deploying stents in conjunction with such procedures.

Typical coronary angioplasty includes advancing a balloon catheter into a patient's coronary artery where the balloon on the catheter is positioned within the stenotic or diseased region of the patient's artery to open up the arterial passageway and thereby increase the blood flow there through. The balloon is inflated with a radiopaque liquid such as a mixture of Renograffin and saline to facilitate fluoroscopic observation of the balloon to ensure properly placement and inflation within the stenosis. After inflation, the balloon on the catheter is deflated and the catheter withdrawn from the diseased arterial region or advanced further into the patient's vasculature for additional treatments or diagnosis.

Very frequently angioplasty procedures include the placement of a stent either during or after the angioplasty procedure to maintain long term patency of the arterial lumen. The balloon catheters used for stent delivery are quite similar to those employed for balloon angioplasty. The balloons on the stent delivery catheters are inflated to expand the constricted stent mounted on the balloon against the vessel wall at the stenotic site. The expanded stent remains at the site and the delivery catheter may be withdrawn after the balloon is deflated.

The mechanical properties of non-compliant or semi-compliant balloons designed for vessel dilatation and/or stent deployment have improved over the years allowing for the use of thinner balloon walls and concomitant lower overall profiles. However, the non-compliant or semi-compliant balloons form wings when in the deflated condition and these wings need to be wrapped tightly around the inner tubular member which extends through the interior of the balloon to present an acceptable profile for advancement through the patient's coronary anatomy. The wrapped balloon may be covered with a protective sheath for storage and transport. The stent may be crimped onto an elastic sheath surrounding the balloon to facilitate a more uniform expansion of the stent. The wings of the balloon are usually heat set in a wrapped condition so they have a tendency to return to the wrapped state upon deflation.

The radiopaque materials (Renograffin) in the inflation fluid used to inflate the balloon, whether for dilatation or stent deployment, are quite expensive, and the viscosity of the inflation fluid is very high, resulting in very slow balloon inflation and deflation times compared with a saline solution not containing radiopaque materials. Efforts in the past to make the balloons on intravascular catheters radiopaque to enable the use of a less viscous non-radiopaque saline solutions have not met with much success. Incorporation of radiopaque materials into the balloon wall usually resulted in unacceptably poor mechanical properties. Coating the balloon with a radiopaque layer usually interfered with balloon folding after inflation and deflation thereof.

Generally, the inflated diameter of the balloon is approximately the same diameter as the native diameter of the body lumen being dilated so as to complete the dilatation but not over expand to the point of damaging the artery wall.

If the balloon on a dilatation catheter or stent delivery catheter is not properly placed during a dilatation or stent delivery, the inflation of the balloon and stent against the vessel wall may cause damage to the adjacent arterial regions which are not diseased. Placement of the balloon at the stenotic site is frequently difficult because the balloon itself is not radiopaque, so the operator does not have the precise locations of the balloon, the working length of the balloon and the stent. Radiopaque markers on the inner member of the catheter shaft aid in stent placement but the location of the markers are not a guarantee of the location of the balloon and the stent within the stenosis.

Therefore, what has been needed is a catheter balloon with improved fluoroscopic visibility. The present invention satisfies these and other needs.

SUMMARY OF THE INVENTION

The present invention is generally directed to an inflatable balloon for an intracorporeal catheter and particularly to such a balloon which has a plurality of adjacent, spaced apart and remotely imageable layers either on the interior surface of the balloon or within a wall of the balloon defining, at least in part, an inflation chamber. Preferably, at least a portion of the layers has properties which facilitate remote imaging by fluoroscopic, magnetic resonance based or other suitable imaging systems.

The imageable layers of the balloon are longitudinally oriented and spaced from each other along one length thereof to allow a degree of articulation by the balloon portions having the imageable layers so as to facilitate the longitudinal folding of the balloon, e.g. the formation of a plurality of wings which may be wrapped about a tubular member extending through the inflation chamber of the balloon.

One intravascular catheter which embodies features of the invention is an elongated balloon catheter suitable for dilatation or stent delivery. This catheter has an elongated shaft with proximal and distal shaft sections and a remotely imageable balloon as described above on the distal shaft section. The catheter has at least one lumen extending therein for delivery of inflation fluid from a proximal extremity of the catheter to the interior of the remotely imageable balloon. A guidewire lumen extends at least within the distal shaft section from a distal port in the distal end of the catheter to a location proximal to the balloon.

The remotely imageable balloon is formed of a non-compliant or semi-compliant polymeric material and preferably has a cylindrically shaped working section with a proximately tapered section at the proximal end of the working section and a distally tapered section at the distal end of the working section. The balloon has at least two, and preferably at least three longitudinally oriented and radially spaced apart and remotely imageable layers on the interior surface or within the wall of the working section of the balloon. The spacing between remotely imageable coextensive layers is relatively (with respect to the imageable layer) non-imageable and the wall thickness thereof is sufficiently less than the wall thickness of the adjacent portions of the wall having remotely imageable layers to facilitate the requisite articulation between the wall portions having the remotely imageable layers. While in certain preferred embodiments the essentially non-imageable spacing is longitudinally oriented so as to be in line or parallel with the longitudinal axis of the balloon, these essentially non-imageable spacings may be disposed about the longitudinal axis in a variety of orientations to provide a desired deflated balloon shape.

The remotely imageable layers may contain radiopaque agents for fluoroscopic imaging or may contain agents having suitable magnetic susceptibility for MRI. The imageable layers should have a thickness of about 0.0005 inch to about 0.01 inch (mm), preferably about 0.001 inch to about 0.003 inch (mm) for fluoroscopic or magnetic resonance based imaging. The spacing between these imageable layers is sufficient to allow for articulation of the adjacent balloon segments with the imageable layers. The width of the spacing is preferably of the same magnitude as the layer thickness which as referred to above is about 0.0005 inch to about 0.01 inch (mm), preferably about 0.001 inch to about 0.003 inch (mm).

The radiopaque agents may be selected from the group consisting of gold, platinum, tungsten, tantalum, lead and radiopaque salts (e.g. sulfates) of barium. The concentration of the imaging agent in a fluid carrier will depend upon the inherent radiopacity of the material and desired layer thickness but generally can range up to 5:1 by weight. The MRI imaging agent may be one or more materials selected from the group of materials having suitable magnetic susceptibilities for MRI consisting of nitinol (NiTi), niobium, tantalum, zirconium, iridium, iron, nickel, cobalt, rare earth metals and alloys thereof. The concentration of the MRI imaging agent within the layer will depend upon the magnetic susceptibility of the material and the requirements of layer thickness for the balloon wall.

The balloon is formed of a non-compliant or semi-compliant polymeric material. Suitable polymeric materials include polyesters such as polyethylene terephthalate (PET), polyamides such as Nylon, thermoplastic or thermoelastic polyurethane or polyesters.

The balloon embodying features of the present invention is preferably constructed with the desired remotely imageable layers formed or otherwise applied to all or part of the working section of the balloon by suitable methods including those known in the art. These methods include spraying a polymeric carrier with one or more remote imaging agents onto the inner surface of the balloon. The non-imageable spacing between the layers may be formed by applying a resist to the non-imageable areas of the balloon interior. Other methods include coating at least part of the interior of the working section of the balloon and mechanically, chemically, or by laser application, removing all or part of the applied imageable coating from the desired regions between the imageable layers to facilitate articulation between the imageable portions of the balloon.

The imageable layers may be on the interior surface of the balloon as described above or formed within the wall of at least part of the working section of the balloon by forming a first layer of the working section, applying the remotely imageable layers to a surface of the first layer and then applying to or forming on the surface of the first layer having the imageable layers a second layer of the balloon working section. Other methods may be used to form the remotely imageable balloon.

Another embodiment of the invention includes elastomeric or inelastic material combined within the balloon or as a layer adjacent to the balloon. Such embodiments could combine the properties of known balloons with the imaging properties available in this invention. Such properties include, but are not limited to, better inflation and deflation characteristics.

The balloon of this invention provides for improved imaging properties in the balloon. Additionally, the balloon's layered manufacturing allows for specific placement of the radiopaque materials. These and other advantages of the invention will become more apparent from the following detailed description of the invention and the accompanying exemplary drawings.

BRIEF DESCRIPTION OF THE DRAWINGS

FIG. 1 is an elevational view, partially in section, of a balloon catheter, which embodies features of the invention, showing a balloon in a partially expanded state.

FIG. 2 is a transverse cross sectional view of the catheter of FIG. 1 taken along lines 2—2.

FIG. 3 is a transverse cross sectional view of the catheter of FIG. 1 taken along lines 3—3.

DETAILED DESCRIPTION OF THE INVENTION

Figure 5:
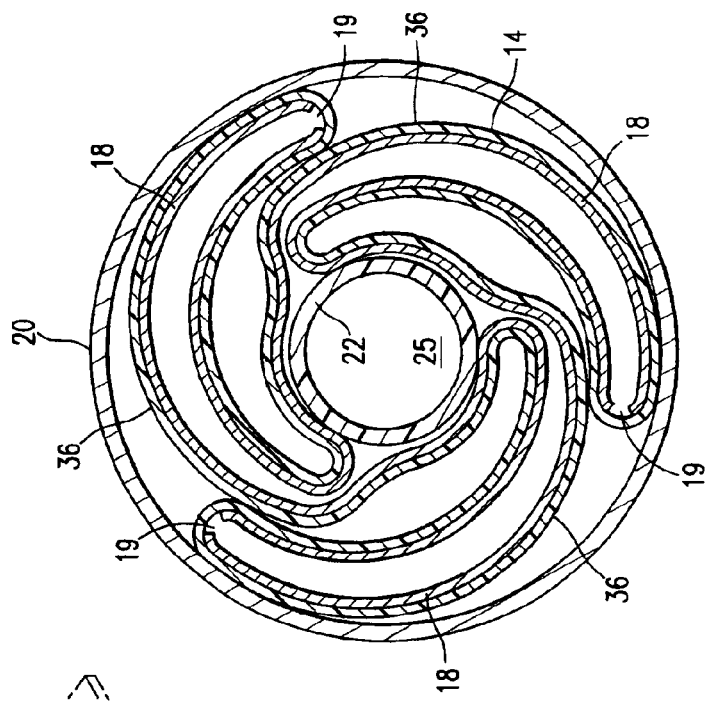
FIG. 5 is a transverse cross-section of the working section of the balloon in a folded condition with a balloon expandable stent mounted about the folded balloon.
Figure 4:
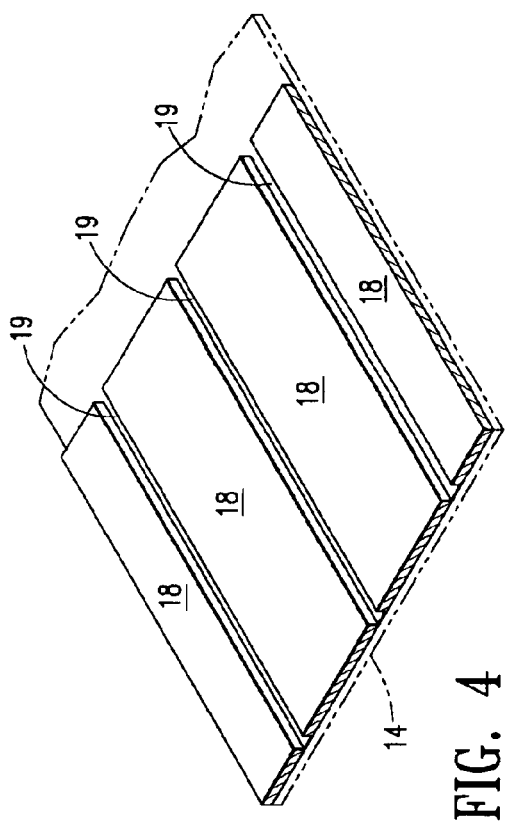
FIG. 4 is a perspective view of the working section of the balloon (shown in phantom) which has been slit longitudinally and laid flat to illustrate the imageable layers on the interior surface of the balloon.

As shown in FIGS. 1–5, the catheter 10 embodying features of the invention generally includes an elongated catheter shaft 11 having a proximal shaft section 12 and a distal shaft section 13, an inflatable balloon 14 having a working section 15 mounted on the distal shaft section 13, and an adapter 17 mounted on the proximal section 12 to direct inflation fluid to the interior of the inflatable balloon 14. Balloon 14 has a plurality of spaced apart remotely imageable layers 18 on the interior surface of the balloon 14. The spacings 19 separate the imageable layers 18 are between A stent 20 is schematically shown mounted about balloon 14.

The catheter shaft 11 has an outer tubular member 21 and an inner tubular member 22 disposed within the outer tubular member and defining, with the outer tubular member, annular inflation lumen 23. Inflation lumen 23 is in fluid communication with the interior chamber 24 of the inflatable balloon 14. The inner tubular member 22 has an inner lumen 25 extending therein, which is configured to slidably receive a guidewire 26. The guidewire 26 facilitates advancement of the catheter 10 through a patient's vasculature to the desired intracorporeal location where the therapeutic or diagnostic procedure is to be performed. The distal extremity 27 of the inflatable balloon 14 is sealingly secured to the distal extremity of the inner tubular member 22 and the proximal extremity 28 of the balloon 14 is sealingly secured to the distal extremity of the outer tubular member 21.

Balloon 14 is formed of a polymeric material, specifically one or more suitable polymeric materials such as thermoplastic or thermoelastic polymeric materials. The deflated single wall thickness is about 0.0005 inch to about 0.002 inch (mm). The imageable layer will be about 0.0005 inch to about 0.01 inch (mm), preferably about 0.001 inches to about 0.003 inches (mm) in thickness.

Figure 6:
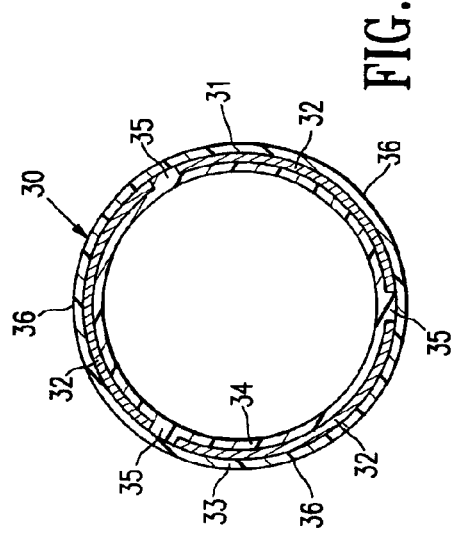
FIG. 6 is a transverse cross sectional view of an alternative embodiment of the catheter shown in FIG. 1 with the remotely imageable layers disposed within the wall of the working section of the balloon.

FIG. 6 illustrates the working section 30 of a catheter balloon 31 having a plurality of imageable layers 32 disposed between outer layer 33 and inner layer 34 of the balloon 31. Elongated essentially non-imageable spacings 35 extend between the layers 32 and are filled by the material of the inner layer 34. The spacings between the imageable layers 32 are preferably non-imageable by remote detectors but they facilitate articulation between the portions 36 of the working section 30 of the balloon 31 The imageable layers 35 may be formed on the outer surface of the inner layer 34 or on the inner surface of the outer layer 33. The imageable layers 35 preferably extend the length of the working section 30; however, the imageable layers may extend only a portion of the working section length.

Although individual features of embodiments of the invention may be shown in some of the drawings and not in others, those skilled in the art will recognize that individual features of one embodiment of the invention can be combined with any or all the features of another embodiment.

What is claimed is:

1. A polymeric balloon having a wall with an interior surface defining at least in part an internal chamber and a plurality of longitudinally oriented, coextensive and spaced apart layers of remotely imageable materials on the interior balloon surface or within a portion of the balloon wall which are configured to facilitate articulation between adjacent spaced apart layers and preferential longitudinal folding of the balloon.

2. The polymeric balloon of claim 1 wherein the spaced apart layers have a thickness of about 0.0005 inch to about 0.01 inch.

3. The polymeric balloon of claim 1 wherein the spaced apart layers have a thickness of about 0.001 inch to about 0.003 inch.

4. The polymeric balloon of claim 1 wherein the wall of the balloon forms a working section of cylindrical shape.

5. The polymeric balloon of claim 3 wherein a proximally tapered section extends from the proximal end of the working section.

6. The polymeric balloon of claim 3 wherein a distally tapered section extends from the distal end of the working section.

7. The balloon of claim 1 wherein at least one of the remotely imageable layers extend along the working length of the balloon.

8. The balloon of claim 1 wherein the wall is formed of at least two layers of polymeric material with the remotely imageable layers disposed between the two layers.

9. The balloon of claim 1 wherein the remotely imageable layers include radiopaque material.

10. The balloon of claim 1 spaced wherein the remotely imageable layers include material imageable by magnetic resonance.

11. The balloon of claim 1 wherein at least one imageable layer has both radiopaque agents and MRI imageable agents.

12. The balloon of claim 1 wherein the spacing between imageable layers is at least 0.0001 inch.

13. The balloon of claim 1 wherein the spacing between imageable layers is at least 0.005 inch.

14. A balloon catheter assembly for stent delivery comprising
   a) a catheter shaft having at least one lumen;
   b) a polymeric balloon which is disposed about and secured to a distal portion of the catheter shaft, which has a wall with an interior surface defining at least in part an internal chamber and which has a plurality of longitudinally oriented, coextensive and spaced apart layers of remotely imageable materials on the interior balloon surface or within a portion of the balloon wall which are configured to facilitate articulation between adjacent spaced apart layers and preferential longitudinal folding of the balloon; and
   c) a stent having a proximal end and a distal end disposed about the balloon.

15. A balloon catheter comprising
   a) a catheter shaft having at least one lumen; and
   b) a polymeric balloon which is disposed about and secured to a distal portion of the catheter shaft and which includes a working section having at least two adjacent wall segments with each segment having longitudinally oriented, coextensive and spaced apart remotely imageable layers which are configured to facilitate articulation between adjacent spaced apart layers and preferential longitudinal folding of the balloon.

16. The balloon catheter of claim 15 wherein the working section of the balloon has a deflated single wall thickness of about 0.001 inches to about 0.0125 inches.

* * * * *